Nov. 18, 1958 G. DE RUITER Plant Pat. 1,771
ROSE PLANT
Filed March 3, 1958
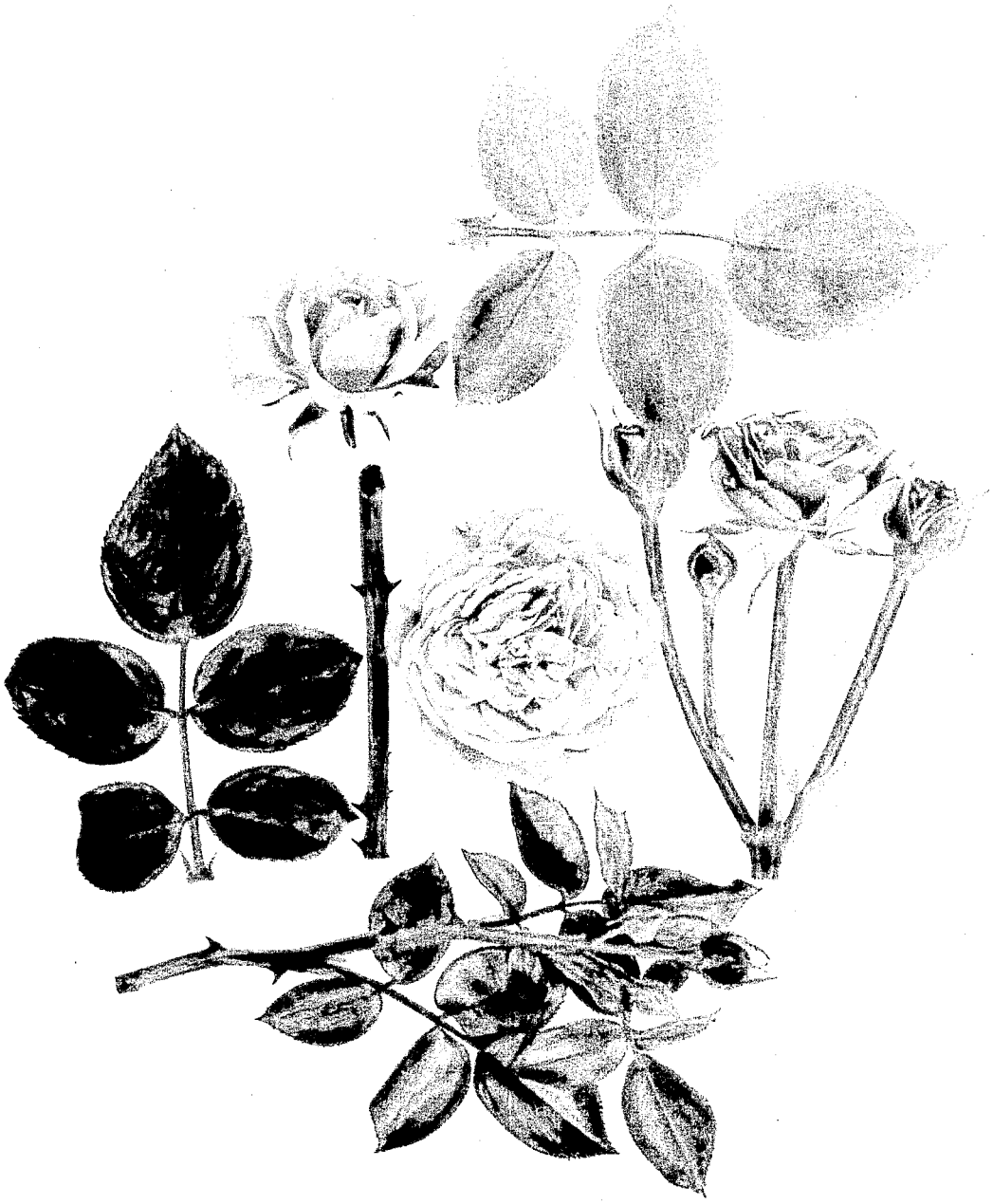
Inventor.
Gerrit de Ruiter
By: Robb & Robb
Attorneys.

United States Patent Office

Plant Pat. 1,771
Patented Nov. 18, 1958

1,771

ROSE PLANT

Gerrit de Ruiter, Hazerswoude, Netherlands, assignor to The Conard-Pyle Company, West Grove, Pa., a corporation of Pennsylvania Application March 3, 1958, Serial No. 718,936

1 Claim. (Cl. 47—61)

The present invention relates to a new and distinct variety of rose plant of the hybrid polyantha class, which was originated by me by crossing the variety "Alain" (unpatented) with an unnamed and unpatented polyantha seedling.

The primary objective of this breeding was to produce a new rose variety which combines therein the most desirable characteristics of the parent varieties. This objective was fully achieved, along with other improvements, as evidenced by the following unique combination of characteristics which are outstanding in my new variety:

(1) Compact habit of growth and bloom, with attendant special suitability for greenhouse pot forcing;

(2) Excellent and disease-resistant foliage;

(3) Uniform and decorative distribution of the blooms on the plant;

(4) Well-formed and long-lasting blooms; and (5) A distinctive Orient Red general color tonality of the blooms.

The foregoing characteristics and distinctions definitely differentiate my new variety from its parents, as well as from all other varieties of its class of which I am aware, and asexual reproduction of the new variety by budding, as performed by me in Holland and as performed on my behalf at West Grove, Pennsylvania, U. S. A., shows that the aforesaid characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the Royal Horticultural Society, except where general color terms of ordinary dictionary significance are obvious:

Type: Hardy; bush; outdoor and greenhouse; seedling; for garden decoration and for greenhouse pot forcing.

Class: Hybrid polyantha.

Breeding: Seedling.

*Seed parent.*—"Alain."

*Pollen parent.*—An unnamed polyantha seedling.

Propagation: Holds its distinguishing characteristics through succeeding propagations by budding.

*Flower*

Locality where grown and observed: West Grove, Pennsylvania, U. S. A.

Flowers borne: Several to stem; in regular, flat clusters; on stems of medium length and normal strength.

Quantity of bloom: Free, outdoors and in greenhouse.

Continuity: Continuous.

Fragrance: Slight. Nature—sweetbriar.

Bud:

*Peduncle.*—Medium length; medium caliper; stiff; rough; with medium number of hairs of Garnet Brown color, Plate 00918. Color—Garnet Brown, Plate 00918.

*Before calyx breaks.*—Size— medium. Form—ovoid; with a conspicuous neck; with foliaceous appendages on the surface of the bud; with stout, entire foliaceous parts extending beyond the tip of the bud equal to ¼ or more of its length.

*As calyx breaks.*—Color—slightly darker than Chrysanthemum Crimson, Plate 824.

*As first petal opens.*—Size—medium. Form—ovoid. Color: outside—slightly darker than Signal Red, Plate 719; inside—Blood Red, Plate 820, overlaid with Purple Madder, Plate 1028 where first exposed to sun.

*Opening.*—Opens up well.

Bloom:

*Size (when fully open).*—From 2¼ inches to 2¾ inches.

*Petalage.*—Double; from 45 to 50 petals; arranged regularly.

*Form.*—Cupped at first and remaining cupped; petals being at first flat and remaining flat at maturity.

Petals:

*Texture.*—Medium thickness; with inside velvety and outside satiny.

*Shape.*—Outer—obovate, with one notch. Intermediate—round obovate, with one notch. Inner—variable, but generally undulate, with one or two notches.

This description of a newly opened flower was made from a rose grown outdoors in the month of September at West Grove, Pennsylvania, U. S. A.:

*Color.*—Outer petal: outside surface—Blood Red, Plate 820, with point of attachment Uranium Green, Plate 63/3; inside surface—Scarlet, Plate 19, with point of attachment Uranium Green, Plate 63/3 which sometimes extends in streaks towards apex of petal. Intermediate petal: outside surface—Currant Red, Plate 821/1, with point of attachment Uranium Green, Plate 63/3; inside surface—Scarlet, Plate 19, with point of attachment Uranium Green, Plate 63/3. Inner petal: outside surface—Turkey Red, Plate 721, with point of attachment Uranium Green, Plate 63/2, and occasionally with streaks of Uranium Green, Plate 63/3 extending towards the apex; inside surface—Scarlet, Plate 19, with point of attachment Uranium Green, Plate 63/3.

This description was made from a rose that was open for three days outdoors in the month of September at West Grove, Pennsylvania, U. S.A.:

*Color.*—Outer petal: outside surface—Currant Red, Plate 821/2, with point of attachment Uranium Green, Plate 63/3; inside surface—Orient Red, Plate 819, with point of attachment Pod Green, Plate 061/3. Inner petal: outside surface—Currant Red, Plate 821/3, with point of attachment Uranium Green, Plate 63/3; inside surface—Orient Red, Plate 819/3, with point of attachment Pod Green, Plate 061/3.

*General color effect.*—Newly opened flower—Orient Red, Plate 819. 3-days open—Orient Red, Plate 819/1.

*Behavior.*—Drop off cleanly.

*Flower longevity.*—On bush in garden—8 days in September. Cut roses grown outdoors and kept at living-room temperatures—6 days in September.

*Reproductive organs*

Stamens: Medium number; arranged regularly about pistils; mixed with petaloids.

Filaments: Many; most with anthers; medium length. Color—Jasper Red, Plate 018 at base, with upper parts Chrome Yellow, Plate 605/1.

Anthers: All open at once; medium size; seldom an anther fused with a petaloid. Color—Buttercup Yellow, Plate 5.

Pollen: Moderate abundance. Color—gold.

Pistils: Medium number.

Styles: Uneven; medium length; medium caliper; bunched.

Stigma: Color—yellow.

Ovaries: All enclosed in receptacle.

Hips: Short; globular; with inconspicuous neck; smooth; walls of medium thickness. Color—reddish.

Sepals: Permanent; medium length; spear-shaped.

Seeds: Medium number; small.

*Plant*

Foliage:

*Leaves.*—Compound of 5 or 7 or more leaflets; abundant; medium size; moderately leathery.

*Leaflets.*—Shape—oval, with apex acuminate. Base—obtuse. Margin—simply serrate.

*Color.*—Mature: upper surface—Spinach Green, Plate 0960; under surface—Sage Green, Plate 000861/1. Young: upper surface—Fern Green, Plate 0862, heavily overlaid with Oxblood Red, Plate 00823; under surface—Oxblood Red, Plate 00823, veined with Fern Green, Plate 0862.

*Rachis (the supporting stem of the compounds leaf).*—Medium caliper. Upper side—hairy. Under side—sparsely prickly.

*Stipules.*—Moderately long; medium width; with moderately short points turning out at an angle of more than 45°.

*Disease resistance.*—Better than average resistance to blackspot and powdery mildew, as determined by comparison with other varieties grown outdoors under the same cultural conditions at West Grove, Pennsylvania; Mentor, Ohio; and Livermore and San Jose, California, U. S. A.

Growth:

*Habit.*—Bushy; upright; much-branched.

*Growth.*—Free.

*Canes.*—Medium caliper.

*Main stems.*—Bright. Color—Spinach Green, Plate 0960/1. Prickles—several; color—Chrysanthemum Crimson, Plate 824, overlying Fern Green, Plate 0862/3. Hairs—none.

*Branches.*—Bright. Color—Spinach Green, Plate 0960/1. Prickles—several; color—Fern Green, Plate 0862/2, with point Oxblood Red, Plate 00823/3. Hairs—none.

*New shoots.*—Bright. Color—Lettuce Green, Plate 861/3, overlaid with Oxblood Red, Plate 00823/3 where exposed to sunlight. Prickles—several; color—Oxblood Red, Plate 00823/3. Hairs—none.

I claim:

A new and distinct variety of rose plant of the hybrid polyantha class, substantially as herein shown and described, characterized particularly as to novelty by the unique combination of its compact habit of growth and bloom, with attendant special suitability for greenhouse pot forcing, excellent and disease-resistant foliage, uniform and decorative distribution of bloom on the plant, well-formed and long-lasting blooms, and the distinctive Orient Red general color tonality of the blooms.

No references cited.